United States Patent [19]
Querns et al.

[11] Patent Number: 5,944,691
[45] Date of Patent: *Aug. 31, 1999

[54] CATHETER HAVING AN EXPANDABLE SHAFT

[75] Inventors: Stephen Querns, Boca Raton; Gitanjali Veroncia Singh, Pembroke Pines, both of Fla.

[73] Assignee: Cordis Corporation, Miami Lakes, Fla.

[ * ] Notice: This patent issued on a continued prosecution application filed under 37 CFR 1.53(d), and is subject to the twenty year patent term provisions of 35 U.S.C. 154(a)(2).

[21] Appl. No.: 08/743,577

[22] Filed: Nov. 4, 1996

[51] Int. Cl.$^6$ .................................................. A61M 29/00
[52] U.S. Cl. ..................... 604/104; 604/164; 604/264; 604/280
[58] Field of Search ..................... 604/104, 256, 604/264, 280

[56] References Cited

U.S. PATENT DOCUMENTS

| | | | |
|---|---|---|---|
| 3,789,852 | 2/1974 | Kim et al. ............................. | 128/347 |
| 4,000,739 | 1/1977 | Stevens . | |
| 4,451,256 | 5/1984 | Weikl et al. . | |
| 4,874,374 | 10/1989 | Kousai ................................. | 604/164 |
| 4,883,468 | 11/1989 | Kousai ................................. | 604/164 |
| 4,994,047 | 2/1991 | Walker et al. ........................ | 604/264 |
| 5,066,288 | 11/1991 | Denirga et al. . | |
| 5,102,401 | 4/1992 | Lambert et al. ...................... | 604/264 |
| 5,176,659 | 1/1993 | Mancini ................................ | 604/280 |
| 5,183,464 | 2/1993 | Dubrul et al. . | |
| 5,248,298 | 9/1993 | Bedi et al. . | |
| 5,256,149 | 10/1993 | Banik et al. . | |
| 5,318,588 | 6/1994 | Horzewski et al. .................. | 606/198 |
| 5,320,611 | 6/1994 | Bonutti et al. . | |
| 5,399,167 | 3/1995 | Deniega . | |
| 5,417,665 | 5/1995 | De La Mata et al. . | |
| 5,445,142 | 8/1995 | Hassler, Jr. . | |
| 5,453,095 | 9/1995 | Davila et al. . | |
| 5,453,099 | 9/1995 | Lee et al. ............................. | 604/282 |
| 5,456,674 | 10/1995 | Bos ....................................... | 604/280 |
| 5,713,864 | 2/1998 | Verkaart .............................. | 604/113 |

*Primary Examiner*—Wynn Wood Coggins
*Assistant Examiner*—Deborah Blyveis
*Attorney, Agent, or Firm*—Dean Garner

[57] ABSTRACT

In accordance with the present invention there is provided a catheter for insertion within the human vasculature. The catheter is capable of being irreversibly expanded from a first diameter to a second diameter. The catheter has an elongated shaft with a distal end, a proximal end and a longitudinal axis extending therebetween. The shaft has a lumen extending therethrough. The lumen has a substantially circular cross section of a first diameter. The shaft has two or more stripes of a substantially rigid material and two or more stripes of a substantially expandable and non-resilient material. The rigid stripes disposed between the expandable stripes. The stripes extend between the distal and proximal ends of the shaft.

18 Claims, 2 Drawing Sheets

CATHETER HAVING AN EXPANDABLE SHAFT

FIELD OF THE INVENTION

The present invention relates to intravascular catheters, such as catheter sheath introducers and guiding catheters used with angioplasty procedures. The present invention has even further relation to such catheters which have an expandable shaft.

BACKGROUND OF THE INVENTION

Catheters, cannulas, or catheter sheath introducers, having hemostasis valves which are mounted on a housing on the end of a catheter are well known in the art. Examples of a catheter sheath introducers are given in U.S. Pat. No. 4,000,739 issued to Stevens on Jan. 4, 1977, U.S. Pat. No. 4,895,565 issued to Hillstead on Jan. 23, 1990 and U.S. Pat. No. 5,417,665 issued to De La Mata et al. on May 23, 1995, all of which are hereby incorporated herein by reference. The catheters have a distal end for insertion into the patient and a proximal end which remains external of the patient. Such catheters are used to facilitate the introduction of other catheters and guidewires into the vascular system of a patient, while minimizing injury to the patient at the access site. For some procedures, such as percutaneous transluminal angioplasty, one or more catheters are inserted into and removed from the patient repeatedly.

The catheter introducer is usually inserted into the femoral or brachial artery of a patient. The presence of the catheter sheath introducer causes the trauma to the body to be limited to only one catheter entering at the body access site. All other catheters and guidewires pass through the catheter introducer, and thus are not traumatic to the body at the access site. Catheter sheath introducers typically have a hemostasis valve located within a housing at the proximal end. The valve can be made from a slit elastomeric partition or membrane. The valve is designed to seal against leakage of blood, as catheters and guidewires of varying diameters are passed therethrough.

When performing interventional procedures, such as PTCA or stent implantation, a guiding catheter is inserted through the catheter sheath introducer and placed adjacent the ostium of the artery. Thereafter, a balloon catheter or the like is inserted through the guiding catheter and delivered to a diseased portion of a coronary artery. During such procedures, the physician often realizes that a larger balloon catheter or stent is needed to treat the particular patient. This may necessitate the need for a larger guiding catheter. In addition to that situation, physicians often will perform diagnostic procedures using relatively small size diagnostic catheters, and thereafter perform interventional procedures with relatively large french size guiding catheters. Both of these procedures often necessitate the need for a larger catheter sheath introducer to accommodate for the larger size catheter. However, exchanging the catheter sheath introducer has many drawbacks, including increased trauma at the insertion site. In addition, exchanging catheter sheath introducers can cause an increase in the procedure time, resulting in additional patient discomfort and additional costs.

There has, therefore, been a need for a catheter sheath introducer, guiding catheter, trocar or the like, which has a shaft that can increase its diameter. There has also been a need to have such a catheter wherein the diameter of the shaft is permanently expanded. By permanently expanding the diameter, friction between the expanded shaft and devices passing therethrough, such as other catheters, decreases. In addition, if the shaft is not permanently expanded, it could damage devices, i.e. stents, balloons etc., as they are passed therethrough, and prevent the removal of such devices out of the shaft. Lastly, a permanently expanded shaft, gives the physician better torque-ability of the devices passing therethrough and allows the physician to do saline flushes. The present invention fulfills such needs.

SUMMARY OF THE INVENTION

In accordance with the present invention there is provided a catheter for insertion within the human vasculature. The catheter is capable of being irreversibly expanded from a first diameter to a second diameter. The catheter has an elongated shaft with a distal end, a proximal end and a longitudinal axis extending therebetween. The shaft has a lumen extending therethrough. The lumen has a substantially circular cross section of a first diameter. The shaft has two or more stripes of a substantially rigid material and two or more stripes of a substantially expandable and non-resilient material. The rigid stripes disposed between the expandable stripes. The stripes extend between the distal and proximal ends of the shaft.

BRIEF DESCRIPTION OF THE DRAWINGS

While the specification concludes with claims which particularly point out and distinctly claim the subject matter forming the present invention, it is believed that the invention will be better understood from the following description of the preferred embodiment taken in conjunction with the accompanying drawings wherein:

DETAILED DESCRIPTION OF THE INVENTION

Figure 1:
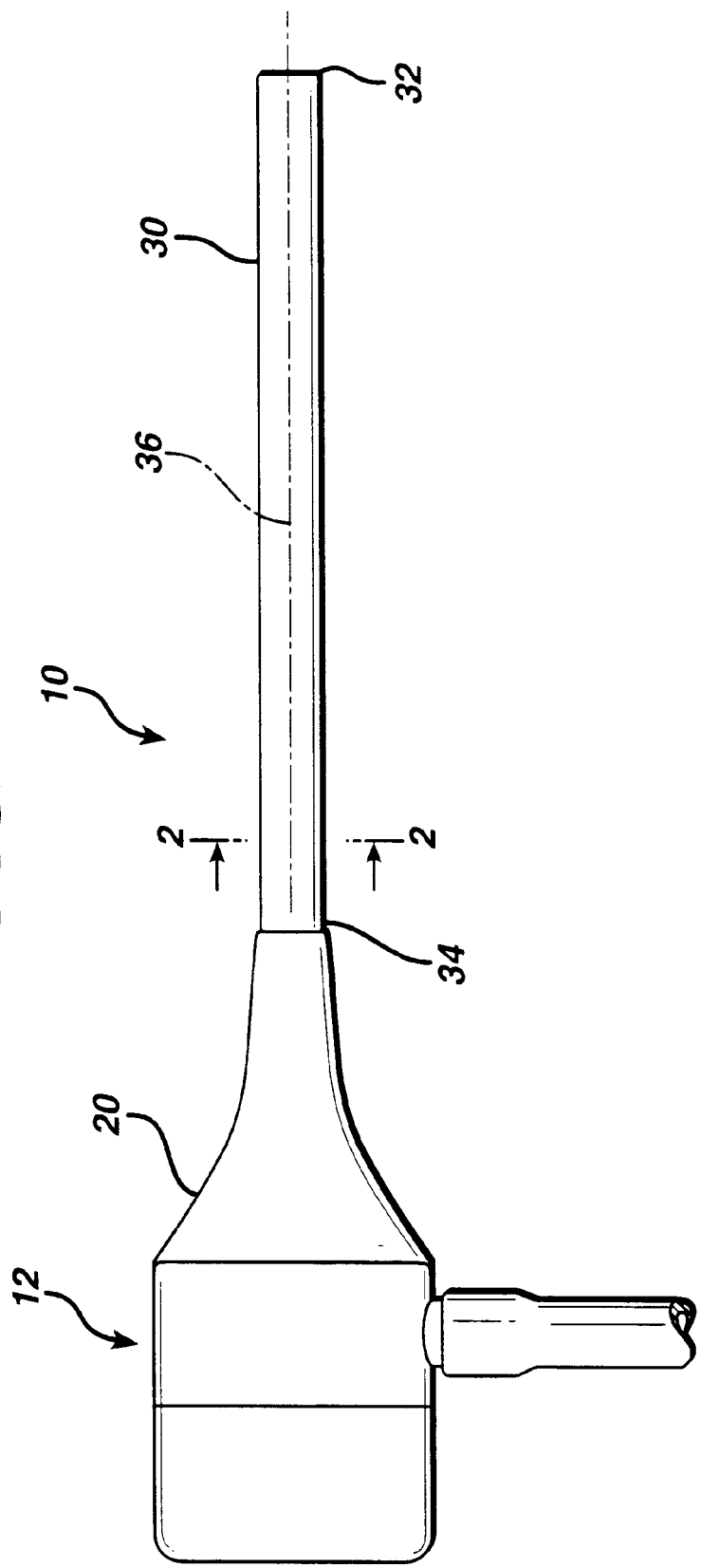
FIG. 1 is a perspective view of a catheter made in accordance with the present invention.

Referring to the drawings wherein like numerals indicate the same elements throughout the views, there is shown in FIG. 1 a catheter 10 made in accordance with the present invention. Catheter 10 is shown as being a catheter sheath introducer, however, as will be appreciated by those skilled in the art, the present invention has equal applicability to many other types of catheters such as guiding catheters and other medical devices such as trocars. All such devices are referred to herein as catheters. Catheter 10 is designed to be inserted into the vessel of a patient and serve as an entrance site for other catheters, guidewires or the like. Catheter 10 includes a proximal end 12 having a rigid housing or hub 20 attached thereto. The housing 20 typically includes an annular valve for access to the lumen of the catheter. A preferred description of a valve is given in the herein before incorporated reference U.S. Pat. No. 5,453,095.

Catheter 10 includes elongated shaft 30. Shaft 30 has a distal end 32, a proximal end 34 and a longitudinal axis 36 extending therebetween. As seen from FIG. 2, the shaft has a lumen 40 extending therethrough. The shaft 30 has initial diameter D1 when initially removed from the package and inserted into the patient. In accordance with the present invention, the shaft is capable of expanding from its initial diameter D1 to a larger diameter D2.

Figure 2:
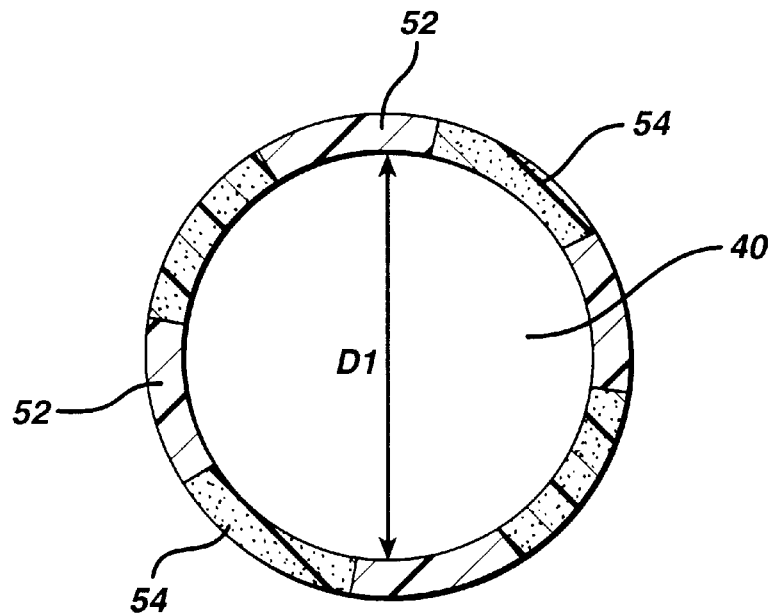
FIG. 2 is a cross-sectional view of the proximal end of the catheter of FIG. 1 taken along line 2—2.
Figure 3:
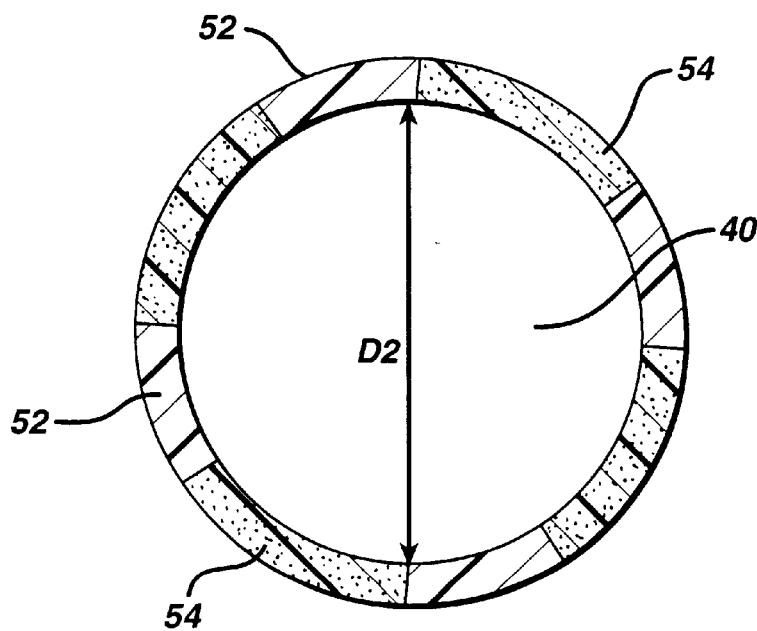
FIG. 3 is a view similar to that shown in FIG. 2 but showing the shaft in its expanded state.

As seen from FIG. 2 and 3, lumen 40 has a substantially circular cross section having a diameter D1. The shaft has two or more stripes 52, preferably 4 as shown in the figures, of a substantially rigid material, and two or more stripes 54, preferably 4 as shown in the figures, of a substantially expandable and non-resilient material. The rigid stripes are disposed between the expandable stripes. The stripes extend between the distal and proximal ends of the shaft. Rigid stripes can be made from any suitable material known in the art including high density polyethylene, rigid polyurethane, high density polyethylene, polyamides, etc. The expandable non-resilient stripes 54 can also be made from any number of suitable materials known in the art including low and ultra-low density polyethylene and modified low and ultra-low density polyethylene, i.e. with maleic anhydrides. It is also preferred that the stripes be equally spaced from each other so that the expansion of the shaft is substantially uniform around its circumference. The number of stripes will depend on the amount of expansion required for the device. If more expansion is needed a larger number of stripes is often needed needed. That is because the expandable non-resilient stripes often have a higher coefficient of friction than the rigid stripes. Stripes 54 need to be large enough to allow for expansion, but small enough so as not to substantially effect the lubricity of the interior of the shaft.

The device is particularly helpful when a physician is performing a diagnostic procedure with a small french size catheter and then goes on to perform an interventional procedure, such as an angioplasty, with a larger french size guiding catheter. After the diagnostic catheter is removed, the physician would insert a dilator into the lumen of catheter 10 through the proximal end. The diameter of the dilator should be about equal to the outside diameter of the guiding catheter. As the physician inserts the dilator into the lumen, the expandable stripes begin to expand while the rigid stripes remain intact. The expandable stripes are non-resilient and yield, beyond their elastic limit, as they are expanded. This prevents the shaft from recoiling to a smaller diameter after the dilator is removed. Thereafter, the physician removes the dilator from the catheter 10 and inserts the new guiding catheter. The rigid stripes provide the necessary rigidity to keep the vessel open and keep the placement of the shaft intact while the expandable stripes allow the shaft to expand.

Shaft 30 can be made from any suitable manufacturing method known in the art including co-extrusion of the rigid and expandable stripes. For applications such as catheter sheath introducers, where the proximal end of the catheter is attached to a device, such as housing 20, the proximal end of the shaft should be expanded to its largest diameter. After which, the proximal end of the shaft can be attached to the housing by any suitable means known in the art such as injection molding or snap fitting. The proximal end of the shaft would be flared to its maximum diameter and then attached to the housing. The housing would be large enough to accommodate the expansion of the shaft.

Although particular embodiments of the present invention have been shown and described, modification may be made to the catheter without departing from the spirit and scope of the present invention. The terms used in describing the invention are used in their descriptive sense and not as terms of limitations.

That which is claimed is:

1. A catheter for insertion within a patient, said catheter has an inside diameter which is capable of being irreversibly expanded from a first diameter to a second diameter, said catheter comprising:
    a. an elongated shaft having a distal end, a proximal end and a longitudinal axis extending therebetween, said shaft having a lumen extending therethrough, said lumen having a substantially circular cross-section having a first inside diameter, and
    b. said shaft comprising two or more arced stripes of a substantially rigid material and two or more arced stripes of a substantially expandable and non-resilient material, said rigid stripes disposed between said expandable stripes, adjacent stripes having ends which are connected to each other, said stripes extending between said distal and proximal ends, said expandable stripes can expand to allow said inside diameter of said shaft to expand, in a substantially uniform manner around a circumference of said shaft, to a second diameter and
    c. wherein said rigid stripes are made from a material chosen from the group comprising: high density polyethylene rigid polyurethane and polyamides.

2. The catheter according to claim 1 wherein said rigid stripes are equally spaced from each other.

3. The catheter according to claim 1 wherein said expandable non-resilient stripes are made from a material chosen from the group comprising: low density polyethylene and ultra-low density polyethylene.

4. The catheter according to claim 1 wherein said catheter is a catheter sheath introducer.

5. The catheter according to claim 4 further including a rigid housing attached to said proximal end of said shaft.

6. The catheter according to claim 5 wherein said housing includes an annular valve.

7. The catheter according to claim 1 wherein said catheter is a guiding catheter.

8. The catheter according to claim 1 wherein said catheter is a trocar.

9. The catheter according to claim 1 wherein said shaft comprises four rigid stripes and 4 expandable non-resilient stripes.

10. A catheter sheath introducer for insertion within an artery of a patient, said catheter has an inside diameter which is capable of being irreversibly expanded from a first diameter to a second diameter, said catheter comprising:
    a. an elongated shaft having a distal end, a proximal end and a longitudinal axis extending therebetween, said shaft having a lumen extending therethrough, said lumen having a substantially circular cross-section having a first inside diameter;
    b. a rigid housing attached to said proximal end of said shaft, said housing including a valve; and
    c. said shaft comprising two or more arced stripes of a substantially rigid material and two or more arced stripes of a substantially expandable and non-resilient material, said rigid stripes disposed between said expandable stripes, adjacent stripes having ends which are connected to each other, said stripes extending between said distal and proximal ends, said expandable stripes can expand to allow said inside diameter of said shaft to expand, in a substantially uniform manner around a circumference of said shaft, to a second diameter.

11. The catheter sheath introducer according to claim 10 wherein said rigid stripes are equally spaced from each other.

12. The catheter sheath introducer according to claim 10 wherein said rigid stripes are made from a material chosen from the group comprising: high density polyethylene, rigid polyurethane and polyamides.

13. The catheter sheath introducer according to claim 10 wherein said expandable non-resilient stripes are made from a material chosen from the group comprising: low density polyethylene and ultra-low density polyethylene.

14. The catheter sheath introducer according to claim 10 wherein said shaft comprises four rigid stripes and 4 expandable non-resilient stripes.

15. A trocar for insertion within a patient to perform an endoscopic procedure, said trocar including a shaft having an inside diameter which is capable of being irreversibly expanded from a first diameter to a second diameter, said trocar comprising:

a. an elongated shaft having a distal end, a proximal end and a longitudinal axis extending therebetween, said shaft having a lumen extending therethrough, said lumen having a substantially circular cross-section having a first inside diameter;

b. a rigid housing attached to said proximal end of said shaft; and c. said shaft comprising two or more arced stripes of a substantially rigid material and two or more arced stripes of a substantially expandable and non-resilient material, said rigid stripes disposed between said expandable stripes, adjacent stripes having ends which are connected to each other, said stripes extending between said distal and proximal ends, said expandable stripes can expand to allow said shaft to expand, in a substantially uniform manner around a circumference of said shaft, increasing said inside diameter to a second diameter; and d. wherein said rigid stripes are made from a material chosen from the group comprising: high density polyethylene, rigid polyurethane and polyamides.

16. The trocar according to claim 15 wherein said rigid stripes are equally spaced from each other.

17. The trocar according to claim 15 wherein said expandable non-resilient stripes are made from a material chosen from the group comprising: low density polyethylene and ultra-low density polyethylene.

18. The trocar according to claim 15 wherein said shaft comprises four rigid stripes and 4 expandable non-resilient stripes.

* * * * *